US012796991B2

(12) United States Patent
Lee

(10) Patent No.: US 12,796,991 B2
(45) Date of Patent: Nov. 17, 2026

(54) SCREW-TYPE ELECTRODE COUPLABLE WITH PLUG-TYPE WIRE

(71) Applicant: SAMSUNG LIFE PUBLIC WELFARE FOUNDATION, Seoul (KR)

(72) Inventor: Seunghoon Lee, Seoul (KR)

(73) Assignee: SAMSUNG LIFE PUBLIC WELFARE FOUNDATION, Seoul (KR)

( * ) Notice: Subject to any disclaimer, the term of this patent is extended or adjusted under 35 U.S.C. 154(b) by 1157 days.

(21) Appl. No.: 15/733,546

(22) PCT Filed: Feb. 19, 2019

(86) PCT No.: PCT/KR2019/001990
§ 371 (c)(1),
(2) Date: Aug. 25, 2020

(87) PCT Pub. No.: WO2019/164223
PCT Pub. Date: Aug. 29, 2019

(65) Prior Publication Data

US 2020/0390356 A1 Dec. 17, 2020

(30) Foreign Application Priority Data

Feb. 26, 2018 (KR) ........................ 10-2018-0022792

(51) Int. Cl.
*A61B 5/293* (2021.01)
*A61B 5/00* (2006.01)
(Continued)

(52) U.S. Cl.
CPC .............. *A61B 5/293* (2021.01); *A61B 5/274* (2021.01); *A61B 5/6868* (2013.01);
(Continued)

(58) Field of Classification Search
CPC ..... A61B 5/293; A61B 5/6847; A61B 5/6868; A61B 5/6878; A61B 2562/16;
(Continued)

(56) References Cited

U.S. PATENT DOCUMENTS 3,964,470 A * 6/1976 Trombley ................ A61N 1/05 600/377
4,220,387 A * 9/1980 Biche ..................... A61B 5/273 439/445
(Continued)

FOREIGN PATENT DOCUMENTS

JP 2006-334106 12/2006
JP 2007-325652 12/2007
(Continued)

OTHER PUBLICATIONS

International Search Report corresponding to PCT/KR2019/001990; dated May 20, 2019 (4 pages, including English translation).

*Primary Examiner* — Eun Hwa Kim
(74) *Attorney, Agent, or Firm* — DILWORTH IP, LLC

(57) ABSTRACT

A screw-type electrode capable of being coupled to a plug-type wire may include a first part having a screw thread to easily insert the electrode into the skull of a patient; and a second part connected to the first part and having a predetermined length. The screw thread may be formed on all or part of the first part, and the second part may have a groove to which the plug-type wire is connected.

9 Claims, 5 Drawing Sheets

(51) Int. Cl.
*A61B 5/274* (2021.01)
*A61N 1/05* (2006.01)
*H01B 7/04* (2006.01)

(52) U.S. Cl.
CPC .......... *A61B 5/6878* (2013.01); *A61N 1/0529* (2013.01); *A61B 2562/0209* (2013.01); *A61B 2562/16* (2013.01); *A61B 2562/225* (2013.01); *A61B 2562/227* (2013.01); *H01B 7/048* (2013.01)

(58) Field of Classification Search
CPC .................. A61B 5/274; A61B 1/0529; A61B 2562/0209; A61B 2562/225; A61B 2562/227; A61B 2562/125
See application file for complete search history.

(56) References Cited

U.S. PATENT DOCUMENTS 4,253,721 A * 3/1981 Kaufman ............... A61B 18/08 439/372
6,319,241 B1 * 11/2001 King ........................ A61N 1/05 607/116
6,778,861 B1 * 8/2004 Liebrecht ............. A61C 8/0007 607/51
7,302,298 B2 * 11/2007 Lowry ................. A61N 1/0534 607/116
8,068,892 B2 * 11/2011 Russell ................ A61N 1/0531 600/378
8,231,620 B2 * 7/2012 Mathonnet ......... A61B 18/1492 606/47
9,226,680 B1 * 1/2016 Kendricks ................ A61B 5/28
2004/0147995 A1 * 7/2004 Miazga ................ A61N 1/0551 607/142
2004/0243207 A1 * 12/2004 Olson ...................... A61N 1/05 607/116
2005/0070810 A1 * 3/2005 Kennedy ................ A61B 5/369 128/903
2005/0227197 A1 * 10/2005 Lin .......................... A61C 7/00 433/18
2006/0068649 A1 * 3/2006 Silber .................... A61B 5/282 439/835
2008/0125637 A1 * 5/2008 Geist .................... A61B 5/4893 606/301
2009/0125072 A1 * 5/2009 Neubardt ........... A61B 17/8625 606/301
2011/0112436 A1 * 5/2011 Jones ................... A61B 10/025 29/527.1
2014/0066750 A1 * 3/2014 Piferi ..................... A61B 90/11 600/417
2014/0275927 A1 * 9/2014 Simpson .................. A61N 1/05 600/382
2015/0057564 A1 * 2/2015 Kim ..................... A61B 17/864 606/301
2015/0272466 A1 * 10/2015 Laakkonen ............ A61B 5/274 600/509
2017/0214203 A1 * 7/2017 Cox ....................... H01R 41/00
2017/0265767 A1 * 9/2017 Pernu ..................... A61B 5/274
2017/0348037 A1 * 12/2017 Sexson .............. A61B 17/1617

FOREIGN PATENT DOCUMENTS

KR 10-2015-0024236 3/2015
KR 10-1645852 8/2016
KR 10-1676577 11/2016

* cited by examiner

SCREW-TYPE ELECTRODE COUPLABLE WITH PLUG-TYPE WIRE

CROSS REFERENCE TO RELATED APPLICATIONS

This application is a 35 U.S.C. § 371 national stage application of PCT International Application No. PCT/KR2019/001990, filed Feb. 19, 2019, which claims priority from Korean Patent Application No. 10-2018-0022792, filed Feb. 26, 2018, the contents of which are incorporated herein in their entireties by reference. The above-referenced PCT International Application was published in the Korean language as International Publication No. WO 2019/164223 A1 on Aug. 29, 2019.

TECHNICAL FIELD

The present disclosure relates to a screw-type electrode capable of being coupled to a plug-type wire, and more particularly, to a screw-type electrode which can be inserted into the skull of a patient in order to stimulate a brain or to measure brain signals.

BACKGROUND ART

EEG (Electroencephalography) refers to an examination method for examining the functionality of a brain by analyzing electrical phenomena of the brain. Since the electrical phenomena of the brain are extremely little and complicated, it is more important than anything to accurately and precisely measure brain signals. In general, a process of recoding brain signals may include measuring brain signals on the scalp of a patient, amplifying the measured brain signals through the EEG, and then analyzing the amplified signals.

Such an EEG may be utilized for diagnosing and sorting brain diseases such as epilepsy and evaluating a treatment result. Furthermore, the EEG may be usefully applied to diagnose whether a patient has a focal or structural brain lesion, disturbance of consciousness or the like.

Furthermore, a brain stimulation is also frequently applied, which treats a disease by stimulating the brain of a patient through an electrode directly inserted into the brain of the patient.

In the EEG and the brain stimulation method, it is essential to precisely apply and extract a signal. Therefore, research is being conducted on various techniques for transmitting/receiving a signal to/from the brain of a patient. In particular, it is necessary to minimize inconvenience experienced by a patient during a process of inserting or extracting an electrode into or from the brain of the patient, and to simplify a surgical procedure for inserting or extracting an electrode further than before, thereby further increasing the effect of diagnosis or treatment for the brain disease of the patient.

DISCLOSURE

Technical Problem

One embodiment of the present disclosure intends to provide a screw-type electrode capable of being coupled to a plug-type wire, which can be inserted into the skull of a patient through a simple surgical procedure under local or sleep anesthesia, in order to easily measure a brain signal and to deliver a brain stimulation.

Technical Solution

In accordance with one embodiment of the present disclosure, there may be provided a screw-type electrode capable of being coupled to a plug-type wire.

The screw-type electrode capable of being coupled to a plug-type wire may include a first part having a screw thread to easily insert the electrode into the scalp and skull of a patient; and a second part connected to the first part and having a predetermined length. The screw thread may be formed on all or part of the first part, and the second part may have a groove to which the plug-type wire is connected.

All or part of the first part may be inserted into the skull of the patient, and used to detect a signal on the surface of the brain of the patient or to stimulate the brain of the patient.

The groove formed in the second part may have a polygonal shape, and a separate insertion tool (for example, screw driver) may be used to insert the electrode into the scalp and skull of the patient.

Outer walls of the first and second parts may have gradations marked thereon and divided in predetermined units.

One terminal of the plug-type wire may have a polygonal shape corresponding to the groove of the second part, and the one terminal may include one or more protrusions. The one or more protrusions may be formed to move when the one terminal of the wire is connected to the groove of the second part.

Advantageous Effects

In accordance with the embodiment of the present disclosure, when the screw-type electrode capable of being coupled to the plug-type wire is used, the user may easily insert the electrode into the skull of a patient through a simple surgical procedure (for example, insertion using a screw driver or the like) under local or sleep anesthesia without mechanical heavy equipment such as a drill, compared to the related surgical procedure. In other words, the electrode may be inserted into the skull of a patient with the minimal invasiveness, which makes it possible to precisely acquire EEG, to shorten the surgical process of a user, and to reduce the pain of the patient.

The plug-type wire connected to the inserted electrode may be used to measure EEG of a patient or to precisely deliver a brain stimulus to the patient.

Furthermore, since the electrode and the plug-type wire, inserted into the skull of the patient, are not spaced apart from each other and can be tightly connected to each other, it is possible to minimize (or remove) noise of a signal, compared to the conventional method in which the wire is wound around the electrode.

BEST MODE

Figure 1:
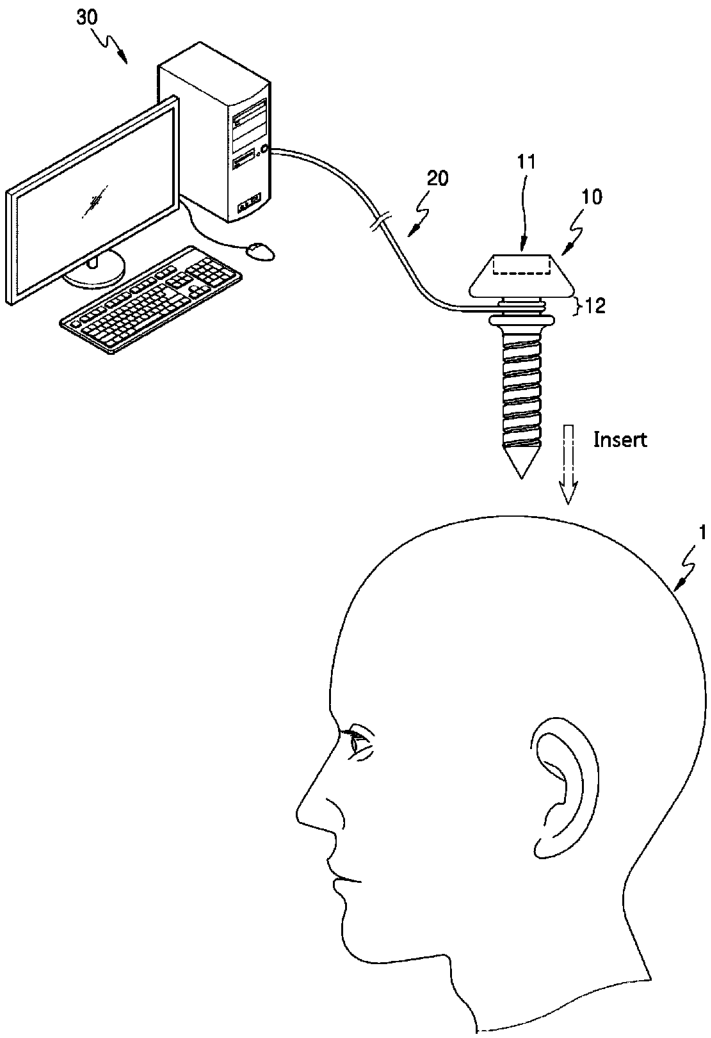
FIG. 1 illustrates that an electrode and wire, which are inserted into a brain, according to the related art are used.

In accordance with one embodiment of the present disclosure, there may be provided a screw-type electrode capable of being coupled to a plug-type wire.

The screw-type electrode capable of being coupled to a plug-type wire may include a first part having a screw thread to easily insert the electrode into the scalp and skull of a patient; and a second part connected to the first part and having a predetermined length. The screw thread may be formed on all or part of the first part, and the second part may have a groove to which the plug-type wire is connected.

All or part of the first part may be inserted into the skull of the patient, and used to detect a signal on the surface of the brain of the patient or to apply a stimulus to the brain of the patient.

The groove formed in the second part may have a polygonal shape, and a separate insertion tool (for example, screw driver) may be used to insert the electrode into the skull of the patient.

Outer walls of the first and second parts may have gradations marked thereon and divided in predetermined units.

One terminal of the plug-type wire may have a polygonal shape corresponding to the groove of the second part, and the one terminal may include one or more protrusions.

The one or more protrusions may be formed to move when the one terminal of the wire is connected to the groove of the second part.

MODE FOR INVENTION

Hereafter, exemplary embodiments of the present disclosure will be described in detail with reference to the accompanying drawings, such that the present disclosure can be easily carried out by those skilled in the art to which the present disclosure pertains. However, the present disclosure can be embodied in various forms, and are not limited to the embodiments described herein. In the drawings, components which have nothing to do with the description will be omitted in order to clearly describe the present disclosure. Throughout the specification, the same components will be represented by like reference numerals.

The terms used in this specification will be briefly described, and the present disclosure will be described in detail.

In this specification, general terms which are widely used at the moment are selected as the terms used herein in consideration of functions in the present disclosure. However, the terms may be changed depending on a technician's intention, a precedent, or an appearance of new technique. In a specific case, a term arbitrarily selected by the present applicant may be used. In this case, the meaning of the term will be described in detail in the corresponding part of this specification. Therefore, the definitions of the terms used herein should not be made by the names of the terms, but be made by the meanings of the terms based on the overall disclosures set forth herein.

Throughout the specification, when an element "includes" a component, it may indicate that the element does not exclude another component unless referred to the contrary, but can further include another component. The terms such as " . . . unit" and "module" in this specification may indicate a unit for processing one or more functions or operations, and the unit may be embodied in hardware, software or a combination of hardware and software. Throughout the specification, when one element is referred to as being 'connected to' or 'coupled to' another element, it may not only indicate that the former element is directly connected or coupled to the latter element, but also indicate that the former element is connected to the latter element with another element interposed therebetween.

The term "user" used in the entire specification may indicate a clinician as a medical expert, but the present disclosure is not limited thereto.

Hereafter, the present disclosure will be described in detail with reference to the accompanying drawings.

Figure 2:
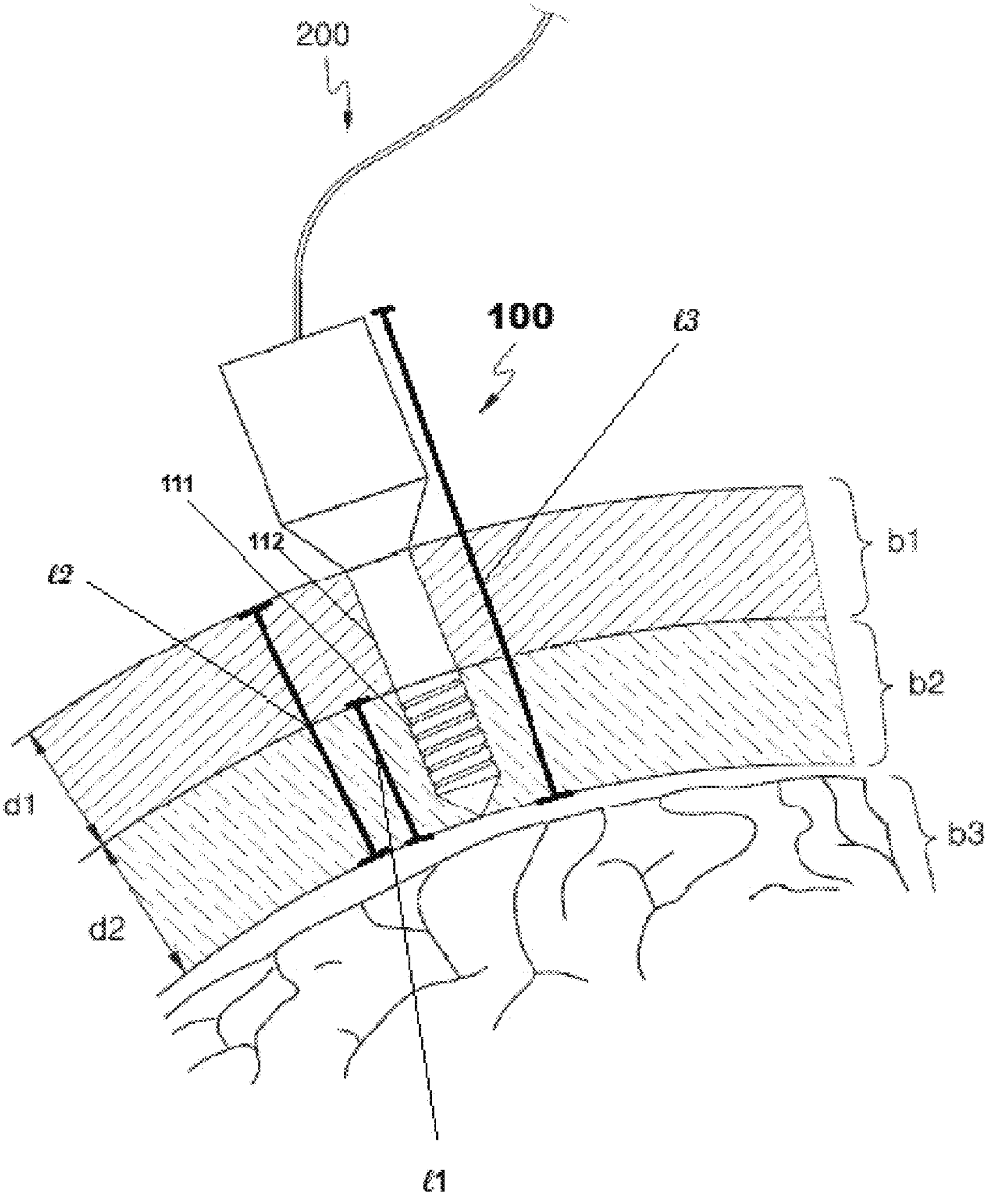
FIG. 2 illustrates that an electrode in accordance with an embodiment of the present disclosure is used.

FIG. 1 illustrates that an electrode and wire, which are inserted into a brain, according to the related art are used, FIG. 2 illustrates that an electrode in accordance with an embodiment of the present disclosure is used, FIGS. 3A and 3B are a side view and perspective view of the electrode in accordance with the embodiment of the present disclosure, and FIG. 3C illustrates a wire in accordance with the embodiment of the present disclosure. FIGS. 4A and 4B are a side view and perspective view of an electrode in accordance with another embodiment of the present disclosure, and FIGS. 5A and 5B illustrate gradations marked on the electrodes in accordance with the embodiments of the present disclosure.

As illustrated in FIG. 1, an electrode 10 for stimulating a brain or measuring brain signals according to the related art has a wire 20 as a signal line wound therearound. In other words, as illustrated in FIG. 1, the electrode 10 may be a screw-shaped electrode to be inserted into the skull of a patient 1, and have a curved shape 12 formed on a pillar thereof, such that the wire 20 is wound around the curved shape 12. According to the related art, the wire 20 is simply wound around the curved shape 12 of the electrode 10, and used for measuring brain signals through a computing device 30 or the like. Thus, a gap is formed between the electrode 10 and the wire 20, thereby frequently generating noise of a signal. In other words, the electrode 10 and the wire 20 may not be completely coupled to each other. Furthermore, although the electrode 10 and the wire 20 are coupled to each other, a gap may be formed between the electrode 10 and the wire 20 as a patient moves during a process of a surgical procedure or diagnosis. In this case, a signal may be incorrectly applied to the brain, or noise may be contained in a signal to be received from the brain.

A screw-type electrode capable of being coupled to a plug-type wire in accordance with an embodiment of the present disclosure can solve the above-described problems.

Referring to FIG. 2, a screw-type electrode 100 capable of being coupled to a plug-type wire 200 in accordance with the embodiment of the present disclosure may be penetrated into the scalp (e.g. area b1 of FIG. 2) of a patient, and inserted into the skull (e.g. area b2 of FIG. 2) as close to the dura mater just below the skull as possible. In other words, the electrode 100 in accordance with the embodiment of the present disclosure may be inserted to reach the area right over the cerebrum (e.g. area b3 of FIG. 2. Of the patient. The electrode 100 in accordance with the embodiment of the present disclosure may include first and second parts which are manufactured to have various lengths. For example, since patients have different scalp thicknesses d1 and skull thicknesses d2 depending on the ages or innate body structures of the patients, a user may check the scalp thickness of a patient through an image (ex. CT, MRI image or the like) acquired for the patient in advance, select an electrode 100 suitable for the scalp thickness of the patient, and utilize the electrode 100 for a surgical procedure. Furthermore, the user may previously determine and acquaint a depth to which the electrode needs to be inserted into the patient, based on the image for the patient. By inserting the electrode to the previously determined depth, it is possible to prevent an unnecessary waste of time during a surgical procedure. Therefore, the first and second parts of the electrode 100 in accordance with the embodiment of the present disclosure may be manufactured to have various lengths in advance. For example, the electrode 100 may include a screw thread portion 111 having a screw thread formed thereon. The screw thread portion 111 may have a length l1 corresponding to a skull thickness d2 of the patient. The electrode 100 may further include a smooth part 112 having no screw thread formed thereon. The smooth part 112 may have a length (l2 minus l1) corresponding to a scalp thickness d1 of the patient, where length l2 is the length of the first part 110 of the electrode 100, as shown in FIG. 3A and described below. The electrode 100 may have an entire length l3.

Figure 3:
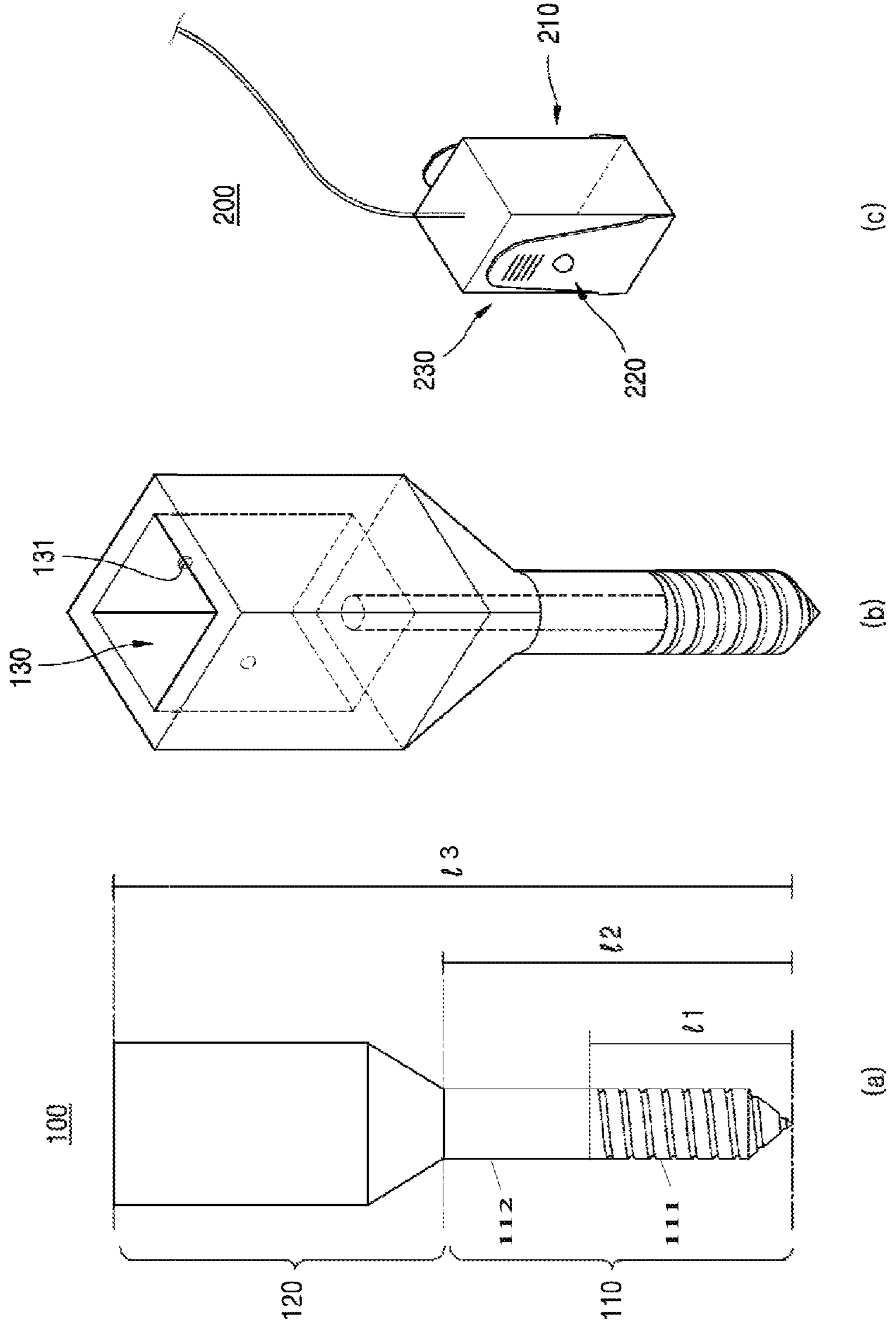
FIGS. 3A and 3B are a side view and perspective view of the electrode in accordance with the embodiment of the present disclosure.
FIG. 3C illustrates a wire in accordance with the embodiment of the present disclosure.

Referring to FIG. 3, the screw-type electrode 100 capable of being coupled to the plug-type wire 200 in accordance with the embodiment of the present disclosure may include a first part 110 having a screw thread for facilitating insertion into the skull 1 of a patient and a second part 120 connected to the first part 110 and having a predetermined length. The screw thread may be formed on all or part of the first part 110, and the second part 120 may have a groove 130 which can be connected to the plug-type wire.

Referring to FIG. 3A, the first part 110 of the electrode 100 may include a screw thread portion 111 having the screw thread formed thereon and a smooth part 112 having no screw thread formed thereon. For example, the length l1 of the screw thread portion 111 may range from 9.6 to 13 mm. Furthermore, the length l2 of the first part 110 may range from 13 to 21 mm. As shown, the smooth part 112 having no screw thread formed thereof may have a length designated by 12 minus 11, where 12 minus 11 is the difference between the length l1 of the screw thread portion 111 and the length l2 of the first part 112. The entire length l3 of the electrode 100 may range from 22.8 to 30.8 mm. Such range values are only examples for description, and not limited thereto. In other words, the above-described range values may be differently decided according to the purpose of use (for example, diagnosed part and surgery purpose) of the electrode 100. As described above, various sizes of electrodes selected by the user according to individual patients may be used.

Furthermore, all or part of the first part 110 may be inserted into the skull of a patient, and used to detect a signal on the surface of the brain of the patient or to apply a stimulus to the brain of the patient. The electrode 100 may additionally include a load for detecting a signal from the brain of a patient or applying a stimulus to the brain. Such a load may be vertically formed from one end of the wire 200 toward a terminal of the electrode 100. Furthermore, the load may be formed in such a shape that the thickness thereof increases from the wire 200 toward the terminal of the electrode 100 (for example, a cylindrical shape with a trapezoidal cross-section). Through such a load on which an electromagnetic influence is minimized, a signal can be transmitted to or received from the brain of a patient more precisely and accurately than in the related art.

According to an embodiment of the present disclosure, the second part 120 may have the groove 130 to which the plug-type wire can be connected, and the groove 130 may have a polygonal shape (for example, triangle or the like). As illustrated in FIG. 3, the second part 120 may have the groove 130 to which one terminal of the wire can be coupled. The user may easily connect the electrode 100 and the wire 200 by inserting the electrode into the skull of the patient, and then inserting one terminal of the wire 200 into the groove 130 formed on the electrode. The connection (coupling) between the electrode 100 and the wire 200 is effective in that the electrode 100 and the wire 200 may not be moved but fixed to the initial installation position, even though a patient moves during a surgical procedure or EEG monitoring or an impact is applied to the electrode 100 or the wire 200 from the outside.

The groove of the second part 120 may have one or more holes 131 for fixing the wire 200. As illustrated in FIG. 3B, the holes 131 may be formed in a line on one or more surfaces of the inner wall of the upper portion of the second part 120. Furthermore, the holes 131 may be formed in two or more lines along the entire surfaces of the inner wall of the second part 120. As the number of the holes 131 and the number of arrangement lines of the holes 131 are increased, the wire 200 and the electrode 100 may be more tightly coupled. Similarly, the one terminal of the wire 200 may have one or more protrusions 220 formed thereon.

FIG. 3C illustrates that one terminal 210 of the wire 200 is formed in a square pillar shape. However, the one terminal 210 of the wire 200 may be formed in a bent shape such as an L-shape. In other words, the plug shape of the one terminal 210 of the wire 200 may be manufactured in various shapes such as a square pillar shape and a bent shape such as an L-shape. According to the patient's posture during diagnosis or treatment, the surgical procedure to be performed, and the location of the electrode to be inserted into the head, a wire having a terminal formed in a square pillar shape or L-shaped plug shape may be used.

In accordance with an embodiment of the present disclosure, a separate insertion tool may be used to insert the electrode 100 into the skull of the patient. For example, the user may easily insert the electrode 100 into the skull of the patient, using a simple insertion tool such as a screw driver other than a drill which is mechanical heavy equipment. Since the first part 110 of the electrode 100 in accordance with the embodiment of the present disclosure has the screw thread for facilitating the insertion, the user may relatively easily insert the electrode 100 into the skull of the patient. Such an insertion tool may have a shape corresponding to the polygonal groove formed in the second part 120. For example, when the second part 120 has a rectangular groove as illustrated in FIG. 3, the user may easily insert the electrode 100 into the patient using a rectangular wrench, a rectangular screw driver or the like.

In accordance with the embodiment of the present disclosure, the one terminal 210 of the plug-type wire 200 may have a polygonal shape corresponding to the groove 130 of the second part 120, and include one or more protrusions 220. As described above, the one terminal 210 of the wire 200 has the same shape as the groove 130 of the second part 120 so as to be coupled and fixed to the second part 120. When the groove 130 of the second part 120 has a rectangular shape as illustrated in FIG. 3, the one terminal 210 of the wire 200 may also have a rectangular shape.

According to an embodiment of the present disclosure, the one or more protrusions 220 may be formed to move when the one terminal 210 of the wire 200 is connected to the groove 130 of the second part 120. For example, the protrusion 220 may be a ball bearing which can be moved in case of contact or an elastic member which is bent in a convex shape. In other words, when the one terminal 210 of the wire 200 is connected to the groove 130 of the second part 120, the protrusion 220 may be moved. Thus, the protrusion 220 may be easily coupled to the hole 131. Furthermore, the one terminal 210 of the wire 200 may additionally have a knob 230 for attaching/detaching the protrusion 220 coupled to the hole 131. By pressing the knob 230, the user may form a gap between the protrusion 220 and the hole 131, such that the protrusion 220 can be easily separated from the hole 131.

Figure 4:
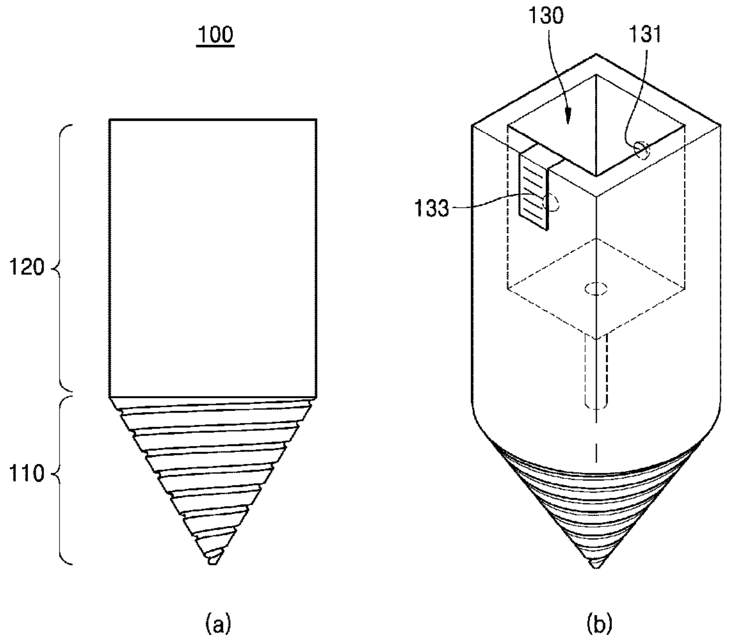
FIGS. 4A and 4B are a side view and perspective view of an electrode in accordance with another embodiment of the present disclosure.

FIG. 4 illustrates an electrode 100 having a different shape from that of FIG. 3. Referring to FIG. 4, a second part 120 connected to a first part 110 having a screw thread may have a cylindrical shape. The second part 120 may have a groove 130 to be coupled to one terminal 210 of a wire, and additionally include a knob 133 for helping a user to attach/detach a protrusion 220 coupled to a hole 131 of the second part 120. As the knob 133 is pressed by the user, the protrusion 220 may be pushed from the hole 131, and thus easily separated from the hole 131. The knob 133 may also be provided on the structure illustrated in FIG. 3B.

Figure 5:
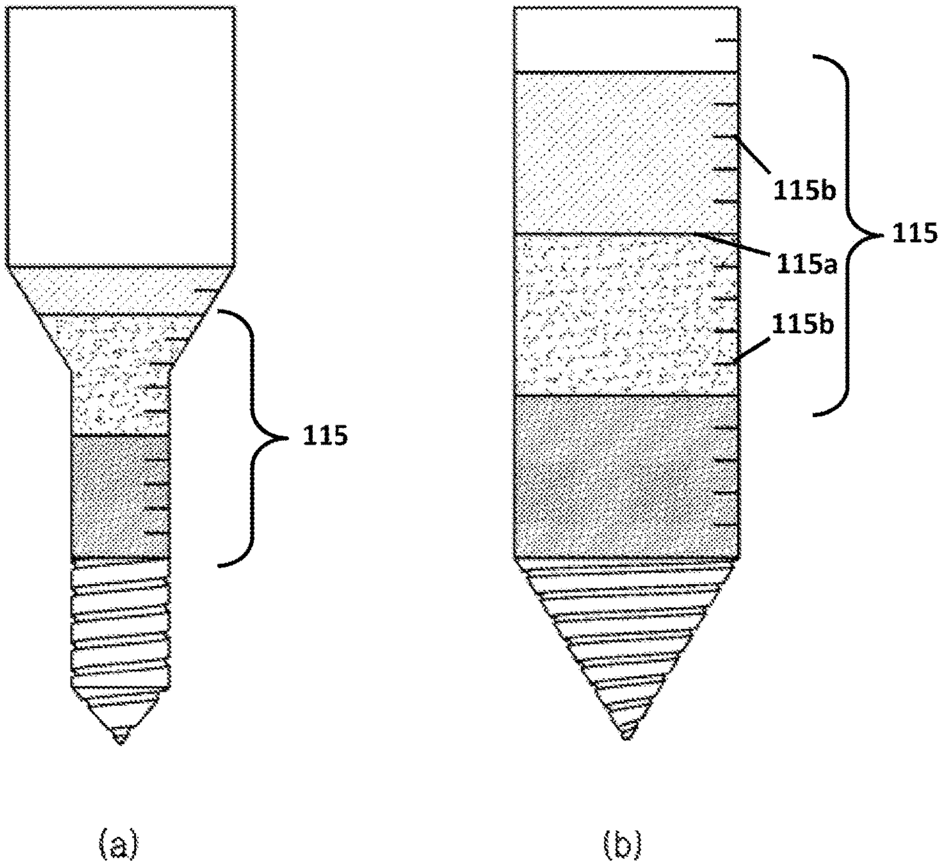
FIGS. 5A and 5B illustrate gradations marked on the electrodes in accordance with the embodiments of the present disclosure.

According to an embodiment of the present disclosure, the first and second parts 110 and 120 may have gradations 115 marked on outer walls thereof and divided in predetermined units. Referring to FIG. 5, the gradations 115 may be successively marked on the outer walls of the first and second parts 110 and 120 while divided in predetermined units. For example, the gradations 115 may be successively marked in units of 1 mm, 0.1 inch, or 0.001 feet. Such gradations 115 may be divided and marked in units of 5. For example, when the gradations 115 correspond to units of 5 as illustrated in FIGS. 5A and 5B, the gradations 115 may be marked as longer gradations 115*a* to be distinguished from the other gradations 115*b*. The longer gradations 115*a* which are spaced and marked in units of 5 may be marked as thicker gradations or marked in different color, compared to the other gradations. For example, when the other gradations have a thickness of 0.5 mm, the longer gradations may have a thickness of 1.5 mm. When the other gradations are marked in black, the longer gradations may be marked in different color such as red or blue. Furthermore, the character (for example, number or the like) of a depth value indicating the depth to which the electrode is inserted may be marked with the corresponding gradation 115. Therefore, when inserting the electrode 100 into the skull of a patient, the user may intuitively recognize how much the electrode 100 is inserted.

According to another embodiment of the present disclosure, the outer walls of the first and second parts 110 and 120 may be coated in different colors. For example, as illustrated in FIGS. 5A and 5B, the outer walls of the first and second parts 110 and 120 may be coated in different colors according to depth values, in order to intuitively indicate the depth value to which the electrode 100 is inserted into the skull of the patient. The user may insert the electrode 100 into the skull of the patient while checking the visible colors on the outer walls of the electrode 100, and thus intuitively predict (estimate) how much the electrode 100 is inserted. As a result, it is possible to effectively block the possibility that an unnecessary complication, which may occur when the electrode 100 may pierce the dura mater or brain, will be developed, and to significantly improve the convenience of a surgical procedure. Since obstacles such as the scalp and skull are present during EEG acquisition, the EEG requires a method for accurately and precisely measuring brain signals while overcoming such obstacles. SDG (Subdural Grid) insertion, which is currently performed among epilepsy surgeries, accompanies craniotomy. Thus, a patient is exposed to a risk such as haemorrhage or infection. For all patients who need an invasive EEG test, the electrode insertion in accordance with the embodiment of the present disclosure may not replace the SDG insertion. However, when the electrode can be inserted less invasively than in the SDG insertion in order to acquire clinical information on a patient through EEG monitoring or brain stimulation, or to treat a disease, it may be very meaningful in a clinical aspect.

When the screw-type electrode capable of being coupled to the plug-type wire in accordance with the embodiment of the present disclosure is used, spatial resolution may be improved more than in scalp EEG according to the related art, and the user can perform a surgery on a patient less invasively than in the SDG insertion. In other words, the time required for the surgical procedure can be shortened, and the risk for a patient can be reduced much more than the existing SDG insertion. In accordance with the embodiment of the present disclosure, the user may easily insert the electrode into the skull of a patient through a simple surgical procedure (for example, insertion using a screw driver or the like) under local or sleep anesthesia, compared to the SDG insertion under general anesthesia. In particular, the electrode can be fixed to the inside of the skull without extensive incision for the scalp, and the plug-type wire can be inserted into the electrode. Therefore, the electrode may be easily attached/detached during a surgical procedure, diagnosis or treatment process.

In other words, in accordance with the embodiment of the present disclosure, the electrode may be inserted into the skull of a patient with the minimal invasiveness, which makes it possible to precisely acquire brain signals, to shorten the surgical process of a user, and to reduce the pain of the patient.

Furthermore, the signal line 200 fixedly connected to the inserted electrode 100 may be used to measure a brain signal of a patient or to precisely provide a brain stimulation signal to the patient. Furthermore, since the electrode and the plug-type wire, inserted into the skull of the patient, are not spaced apart from each other and can be fixedly connected to each other, it is possible to minimize (or remove) noise of a signal, compared to the conventional method in which the wire is wound around the electrode.

The contents on the above-described device (for example, electrode) may be applied to the electrode insertion and utilization method in accordance with the embodiment of the present disclosure. Therefore, in relation to the method, the descriptions of the same contents as the contents on the above-described device are omitted herein.

The descriptions of the present disclosure are only examples, and it should be understood that the present disclosure can be easily modified into other specific forms by those skilled in the art to which the present disclosure pertains, without changing the essence of technology or necessary features of the present disclosure. Therefore, it should be understood that the above-described embodiments are only examples in all aspects and are not limitative. For example, components described in a singular form may be distributed and carried out. Similarly, distributed components may be carried out in a coupled form.

The scope of the present disclosure is defined by the following claims rather than the detailed descriptions, and it should be construed that the meaning and scope of the claims and all changes or modifications derived from the equivalents thereof are included in the scope of the present disclosure.

What is claimed is:

1. A screw-type electrode couplable to a plug-type wire, the screw-type electrode comprising:

a first part having a screw thread configured to insert the screw-type electrode into a skull and scalp of a patient, the first part comprising:

a screw thread portion having the screw thread formed thereon, the screw thread portion having a thread portion length with a value in a range of from 9.6 mm to 13 mm corresponding to a skull thickness of the patient, and a smooth part having no screw thread formed thereon, wherein the first part having a first part length with a value in a range from 13 mm to 21 mm and wherein the smooth part having a smooth portion length with a value of the first part length minus the thread portion length such that the smooth portion length corresponds to a scalp thickness of the patient; and a second part connected to the first part and having a predetermined length, the second part having a groove configured to receive a terminal of the plug-type wire, one or more holes positioned on an inner side wall of the groove, and the terminal having one or more corresponding protrusions coupled to and extending outwardly from the terminal, wherein, when the terminal of the plug-type wire is inserted into the groove of the second part of the screw-type electrode, the one or more protrusions of the terminal are configured to deflect such that they can be received by the corresponding one or more holes of the second part, thereby coupling the plug-type wire to the screw-type electrode; and wherein the first part is adapted to at least one of detect a signal on a surface of a brain of the patient or deliver a stimulus to the brain of the patient.

2. The screw-type electrode of claim 1, wherein all or part of the first part is configured to be inserted into the skull of the patient.

3. The screw-type electrode of claim 1, wherein the groove formed in the second part has a polygonal shape, and a separate insertion tool is configured to insert the screw-type electrode into the skull of the patient.

4. The screw-type electrode of claim 1, wherein outer walls of the first and second parts have gradations marked thereon and are divided in predetermined units.

5. The screw-type electrode of claim 3, wherein the terminal of the plug-type wire has a polygonal shape corresponding to the groove of the second part.

6. The screw-type electrode of claim 5, wherein the one or more protrusions include an elastic member having a convex shape.

7. The screw-type electrode of claim 1, wherein the terminal comprises a knob configured to push the one or more protrusions from the respective one or more holes of the groove, thereby allowing the terminal to be detached from the second part.

8. The screw-type electrode of claim 1, wherein the screw type electrode has a length having a value ranging from 22.8 mm to 30.8 mm.

9. The screw-type electrode of claim 1, wherein at least one of the first part and the second part are coated in different colors according to depth values.

* * * * *